United States Patent [19]

Pentz

[11] 4,426,460
[45] Jan. 17, 1984

[54] POLYURETHANES OR ISOCYANURATES FROM ALKOXYLATED HYDROXYMETHYLFURAN

[75] Inventor: William J. Pentz, Cary, Ill.

[73] Assignee: Quaker Oats Company, Chicago, Ill.

[21] Appl. No.: 291,446

[22] Filed: Aug. 10, 1981

[51] Int. Cl.³ ............................................. C08G 18/14
[52] U.S. Cl. .................................. 521/115; 521/116; 521/131; 521/164; 521/166; 521/174; 528/48; 528/53; 528/73; 544/193
[58] Field of Search ................ 521/115, 116, 131, 164, 521/166, 174; 528/48, 53, 73; 544/193

[56] References Cited
U.S. PATENT DOCUMENTS 4,219,485  8/1980  Dunlop ................................. 528/73
4,316,935  2/1982  Moss .................................... 521/174

Primary Examiner—Maurice J. Welsh
Attorney, Agent, or Firm—James T. FitzGibbon

[57] ABSTRACT

Improved rigid urethane and isocyanurate foam compositions having improved fire resistance are described. The urethane foams are based on furan compositions having the formula:

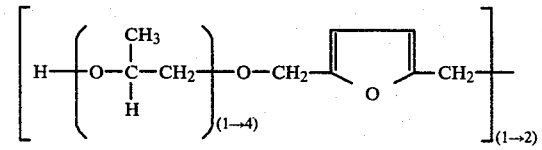

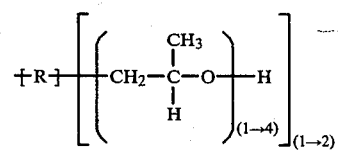

wherein R =

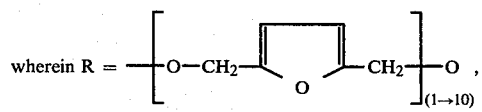

R = 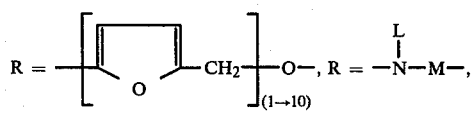 , where L is lower alkyl or M, and M is

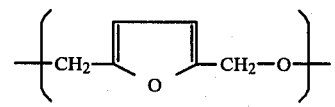

R =

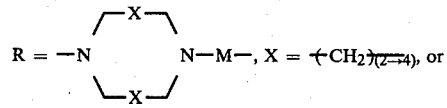

R = 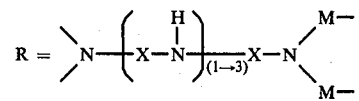

and from about 100% to about 500% of a stoichiometric amount of a reactive polyisocyanate to produce a foamable composition, and sufficient blowing agent to create a foam having a density from about 1.5 to about 5 pounds per cubic foot. The product has improved fire resistence. The disclosure also described the method of decreasing the flame hazard potential of a rigid foam by adding two urethane or isocyanurate foaming ingredients the appropriate amount of one or more of the compositions listed above. The polymers described are chiefly made from adding propelyne oxide to bis (hydroxymethyl) furan.

22 Claims, No Drawings

POLYURETHANES OR ISOCYANURATES FROM ALKOXYLATED HYDROXYMETHYLFURAN

The present invention relates generally to novel chemical compositions and methods, and more particularly, to modified furan-based compositions, to chemical compositions made with such modified furan-based compositions, and to methods of making novel furan-based chemical compositions.

In recent years, polyurethane and polyisocyanurate foams have become very valuable products in industry. Generally, these foam products are low density for use in building products and like applications wherein their excellent thermal insulating capabilities may be taken advantage of. In addition, existing urethane and isocyanurate foams possess excellent dimensional stability, outstanding structural strength, and have other advantages and characteristics known to those skilled in the art.

However, as with all organic resinous materials, a characteristic potential drawback is present, and that is, the flammability and smoke and/or noxious gas generation potential of such compositions. As a consequence of the potential dangers involved in combustion of organic resin foams, there have been advanced a number of proposed solutions to the combustion products problems encountered with urethane foams. While some foams, such as expanded polystyrene, are simply too flammable to be used in many applications, othr foams, such as urethanes, are capable of meeting building and other codes when properly formulated.

One common approach has been to incorporate halogen-bearing compounds into the foam product, either as an integral part of one or more of the resins, or as in another addend of some kind. In addition, there has been an effort to seek out and develop starting resinous materials which themselves provide decreased flame hazard potential and/or reduced smoke generation under conditions of combustion. Normally, in the industry, foams are for this purpose rated according to several standard tests. One such test, known as the ASTM E-84 test, relates to the travel of flame along a horizontal surface of the foam product when it is placed in a standard tunnel. Another test, commonly known as the 2 foot tunnel test involves similar circumstances. A third test, standardized and sometimes administered by the United States Bureau of Mines, established flame or heat travel through the foam itself.

A still further test, the National Bureau of Standards "NBS" test, basically establishes the density of the smoke generated as a result of foam combustion.

In performance of such tests, an ideal product is one which will not support combustion, and one which forms on its surface a heat insulating non-combustible char which diminishes flame hazard potential in relation to the remaining product. Consequently, an advantageous product is one which does not burn in the absence of flame, one which does not emit toxic or flammable smoke or fumes, one which forms a protective char in the event that it is exposed to flame, and one which resists passage of heat directly therethrough even under conditions of extreme temperature.

In the past, in selecting certain desirable resins for use in the manufacture of urethane foams, furan based products, such as polymers of furfuryl alcohol, and most recently, polymers based on 2,5-bis(hydroxymethyl)furan have been found to be desirable. When urethane foams are made with these starting products, the amount of halogen-containing additives required to obtain certain flame hazard potential ratings is diminished, and as a result, such furan-based products appear to be advantageous when used in making urethane foams.

Aside from the requirement of presenting the lowest possible flame hazard, a desirable component of a urethane foam is one which, when used in a typical commercial urethane system, will be compatible with the isocyanate system used and, which, when engaged in the foam producing reaction, exhibits desirable characteristics. These characteristics include compatibility of the resin with the blowing agent, which at the present time, is almost without exception, a fluorocarbon ("Freon") product. A resin product not compatible with "Freon" is commercially unacceptable.

Another desirable characteristic of a resin system component is that the kinetics of the reaction be such that the urethane foam produced will be a substantially closed cell foam having desirable insulating characteristics. If the foam reaction is one which creates rupturing of cell walls during formation, a product having a large number of open cells will be formed, and such product will have extremely poor heat insulation characteristics and as a practical matter, prohibitive cost. While furfuryl alcohol polymers, including polymers of 2,5-bis(hydroxymethyl)furan have potential advantages, they have suffered in the past from certain drawbacks which include extremely high viscosity, functionality which is less than that which is desired, a tendency to crystallize from the liquid form, and to be incompatible with common blowing agents.

According to the present invention, it has been found possible to modify known furan-based products in a number of ways in order to create new products and classes of products which are useful in making urethane and isocyanurate foams and other useful products.

For example, it is possible to propoxylate 2,5-bis(hydroxymethyl)furan (hereinafter "BHMF"), in order to obtain a product which is of low viscosity, which is fluorocarbon-compatible, and which may be used as a component of a urethane foam of reduced flame hazard potential.

Resins based on higher homologs of BHMF may also be propoxylated to provide modified resins which, although of somewhat increased viscosity, are still compatible with fluorocarbons, and which also are able to improve the flame hazard potential of urethane foams made from them.

For example, a resin resulting from the homopolymerization of BHMF and having a viscosity of 10,000 cps can be propoxylated to attain a viscosity of 6,500 cps and to achieve the required fluorocarbon compatibility, and to create the potential for further viscosity reduction needed to be commercially acceptable. Such propoxylated (hereinafter sometimes "PO") resins have a higher proportion of furan nuclei in relation to propylene oxide constituents than does propoxylated BHMF, and therefore, offer reduced flame hazard potential in the finished urethane foam product. One phase of the present invention is, therefore, the addition of propylene oxide to furan-based components to achieve the desirable combination of fluorocarbon compatibility and reduced flame hazard potential.

Another aspect of the invention relates to propoxylating furfuryl alcohol to a desired degree prior to reacting the furfuryl alcohol ("FA") material with formaldehyde and methylamine. This procedure makes it possible to produce so-called Mannich diols which are more pure than counterpart diols made from FA itself. Such novel chemical products are useful in urethane foams in reducing the flame hazard potential of the final product, as well as being desirable because they may serve as trimerization catalysts in making isocyanurate foam products. These compositions also have inherently reduced viscosity and moreover, are fluorocarbon-compatible. Urethane foams incorporating these products display advantageous properties in several respects.

Yet another type of product made according to the invention is a Mannich triol made by adding propoxylated FA to ammonia and formaldehyde in the presence of an acid. The resulting triols exhibit marginal fluorocarbon compatibility, but have acceptably low inherent viscosity and may be used in urethane foams. They do not exhibit significant activity as a trimerization catalysts.

In view of the fact that urethane foams and components thereof are still capable of further improvement, it is an object of the present invention to provide improved chemical compositions for use in the manufacture of urethane foams.

Another object of the invention is to provide a method of making compositions which are useful in urethane foams.

A still further object of the present invention is to provide a method of making urethane foam intermediates, particularly those which are compatible with fluorocarbon blowing agents used in the production of urethane foams.

A further object of the present invention is to provide materials which are useful in imparting reduced flame hazard potential to urethane and isocyanurate products, including rigid urethane and isocyanurate foam compositions.

Another object of the invention is to provide novel Mannich diols and triols which are suitable for use in urethane and related products.

A still further object of the invention is to provide particular chemical compositions, and methods of making them, including specifically, propoxylated 2,5-bis(hydroxymethyl)furan; propoxylated resins resulting from the homopolymerization of 2,5-bis(hydroxymethyl)furan and Mannich diols and triols resulting from the propoxylation of materials used in Mannich diol and triol synthesis.

Another object of the invention is to provide a family of compounds which are (1) compatible with fluorocarbons, (2) which display reduced viscosity in relation to their unmodified counterparts, and (3) which are useful as components of urethane or isocyanurate foams and other compositions.

A still further object is to provide a method of modifying chemical compositions having the potential to impart reduced flame hazard potential to urethane foam so as to render them more suitable for incorporation into such foam products.

An even further object of the invention is to provide urethane foam products and isocyanate foam products which provide reduced flame hazard potential without the use of halogen-containing additives, or which require a reduced level of such additives to provide a predetermined level of flame resistance.

In addition, it is an object of the present invention to provide a novel component for use in a urethane foam which will have desirable characteristics of compressive strength and friability, as well as desirable reactivity characteristics.

Another object is to provide compositions which impart reduced flame hazard potential foam to products and which are of a viscosity suitable for use with existing equipment rather than being so viscous as to be impractical for use with existing equipment.

Another object of the invention is to provide a polyol composition having secondary hydroxyl groups as reactive sites in order to reduce to a desirable degree the rate of reaction between the isocyanate component and the polyol component during the formation of a urethane product. This, in turn, enables the reaction to be controlled to any desired degree by catalyst selection or by other variables as may be desired by the processor.

The foregoing and other objects and advantages of the invention are achieved in practice by providing novel propoxylated compositions, by providing methods of making compositions using propoxylated, furan-based compositions as starting materials, and by producing rigid urethane and isocyanurate products of reduced flame hazard potential using the foregoing compositions and their derivatives. The manner in which these objects and advantages are achieved in practice will become more clearly apparent when reference is made to the detailed description of the invention set forth below and illustrated by way of the several examples appearing in the specification.

DESCRIPTION OF THE PREFERRED EMBODIMENTS OF THE INVENTION

While the chemical compositions and methods of the invention are capable of a number of uses, and have numerous advantages and characteristics, a description will be made of the manner of making certain novel compositions of the invention Their uses will be illustrated in subsequent examples.

Before referring to the examples in detail, reference will be made to certain abbreviations and other expressions which commonly occur. The composition 2,5-bis(hydroxymethyl)furan is hereinafter referred to as BHMF. Homopolymers of BHMF are referred to a BHMFP. Where BHMF is reacted with one or more moles of propylene oxide, the propoxylated product is referred to as PO-BHMF. Where the BHMF polymer is so reacted, the product is referred to as PO-BHMFP.

The molar equivalent ratios of propylene oxide to the other constituents are respectively referred to as PO:BHMF; PO:BHMFP, etc.

One starting material is basically a homopolymer of BHMF; it is commercially available from the Quaker Oats Company of Chicago, Ill. and is identified as a "Farez" resin. One such typical resin is Farex B-260 which is a polymer of BHMF having a viscosity of 10,000±2,00 cps @ 25° C. This material has a specific gravity of 1.29 @ 25° C., a hydroxyl content of 16–18%, an acid number of 2–5, and contains 1% or less water. The material is a black resin having 2–3% furfuryl alcohol (hereinafter "FA") content and is 85% polyfunctional. This resin includes as its principal constituents three moieties, namely, (I) BHMF, having the structure set forth below:

(II) a homopolymer of BHMF having the structure set forth below:

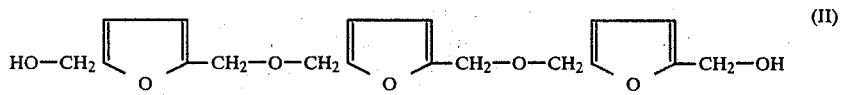

and (III) another polymer of the following structure:

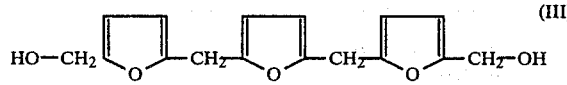

in addition to impurities and perhaps other reaction products of the above compounds.

Compounds II and III above are formed from the homopolymerization of BHMF, and depending upon the nature of the polymerization reaction, include either methylene bridges joining adjacent furan rings, or etherfinic di-methylene linkages joining such rings.

Inasmuch as the present invention concerns the feasibility of propoxylating BHMF, both as a way of developing a novel and useful product per se, and by way of demonstrating that the higher polymers of BHMF may be propoxylated, certain of the examples herein are directed to an illustration of the manner of propoxylating both BHMF and its homopolymers, and mixtures thereof, as well as an analysis of the properties of products made therefrom.

Because as a typical use of the novel compositions of the invention is in the manufacture of rigid urethane and isocynanurate foams, other examples illustrate the use of PO-BHMFP and related compounds in urethane and isocyanurate formations, together with a discussion of the chemical and physical properties of the end products.

Still further examples relate to products known as Mannich diols and Mannich triols, and to the use of such diols and triols. These compositions involve propoxylation of furfuryl alcohol (FA) prior to its reaction with methylamine or ammonia in the presence of formaldehyde and an acid catalyst. Uses of these materials are illustrated in the later examples.

EXAMPLE 1

In this example, it was desired to make the PO-BHMF composition referred to above.

A one liter 3-necked flask equipped with mechanical stirrer, thermometers, propylene oxide ("PO") bubbler tube and a heating mantle was charged with 256 grams (one hole) of 2,5-bis(hydroxymethyl)furan and with 8 grams of sodium hydroxide (0.05 moles hydroxide equivalent) as a catalyst.

The use of sodium hydroxide, potassium hydroxide, and the like are known as catalysts in propylene oxide addition reactions of this kind. Accordingly, their use being known to those skilled in the art, further discussion thereof is not believed necessary, and further description of the use of these materials will not be set forth in the examples.

The mixture was heated to 130° C. under a nitrogen blanket and stirred. Then 214.2 grams of propylene oxide were bubbled into the mixture under atmospheric pressure over a period of 2¼ hours. The product was allowed to cool and was removed from the reaction vessel. After purification, the novel material, sometimes referred to herein as PO-BHMF, but properly identified as 1,1'-[2,5furandiylbis(methyleneoxy)]bis-2-propanol, was postulated to have the chemical structure set forth below:

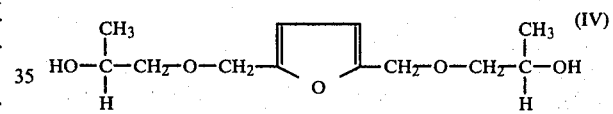

This product, PO-BHMF, was a tan liquid having a viscosity of 770 centipoises ("cps") at 25° C. and a hydroxyl number of about 477.

EXAMPLE 2

This example illustrates how varying the molar equivalent ratio of propylene oxide (PO) to BHMF improves the fluorocarbon compatibility of the resulting compound. Using the above method of adding the PO to the BHMF, a series of PO:BHMF adducts were produced by adding PO to the BHMF until the desired PO:BHMF ratio was achieved, removing a sample, adding more PO to the product until a different PO:BHMF ratio was achieved, and so on. First, 214.2 grams of PO were bubbled into a vessel containing 256 grams (one mole) of BHMF over a period of 2¼ hours. A 203.2 gram aliquat (Sample 1, Table I) was taken and found to have a hydroxyl number of 477 and a viscosity of 770 cps.

To the remaining material was then added 238.3 grams of PO, over a four hour period at 140°-145° C. A 260.9 g sample (Sample 2, Table I) was taken and found to have a hydroxyl number of 335.8 and a viscosity of 300 cps at 25° C.

To the remaining mixture another 213.8 grams of PO was added over a seven hour period at 150°-160° C. The remaining material (Sample 3, Table I) exhibited a hydroxyl number of 225.6 and a viscosity of 200 cps at 25° C.

A propoxylated BHMF product having varying levels of propylene content may be illustrated as follows:

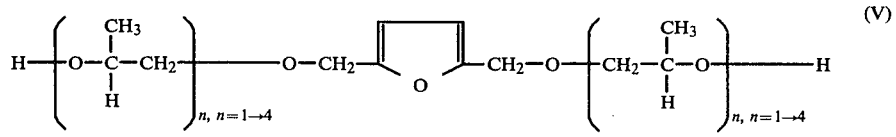

(V)

The following table summarizes molar equivalent ratios of PO:BHMF for each of the samples and their compatibility with a commonly used blowing agent, fluorotrichloromethane ("Freon 11") available from the DuPont Company of Wilmington, Del.

TABLE 1

| Sample | Molar equivalent Ratios of PO:BHMF (OH Equivalent) | Blowing Agent Compatibility, grams Freon 11 per 100 grs of PO—BHMF or "Polyol" |
|---|---|---|
| 1 | 0.92:1 | 46 |
| 2 | 2.7:1 | 65 |
| 3 | 6.54:1 | 80 |

EXAMPLE 3

In this example, it was desired to demonstrate that the "Freon 11" compatibility of various homopolymers of BHMF could be altered by propoxylating them. For this purpose, a series of homopolymers of BHMF had varying levels of BHMF content, and were propoxylated to produce a PO:BHMFP, i.e., a propoxylated polymer of BHMF or BHMFP at a 0.95 or 1.05:1 PO:BHMFP hydroxyl equivalent ratio. The products were prepared using a one-liter Parr reactor equipped with an agitator, a heater, as well as nitrogen and propylene oxide pressure addition capabilities. 450 grams of a BHMFP having a viscosity of 28,000 cps and a BHMF content of 39%, and 3% NaOH, were added to the reactor. The mixture was heated to 125° C. under a nitrogen blanket with the pressure not exceeding 50 psig. Then, propylene oxide was fed under pressure into the reactor to a maximum of 100 psig.

As the propylene oxide (PO) was added, the PO "capped" or served to react with the terminal methylol groups on the BHMFP. When the pressure dropped, additional PO was fed to the reactor. The total PO added was based on the requirement of achieving the desired hydroxyl equivalent, namely, about 95% of the theoretical amount required to react with all terminal methylol groups.

The reaction was carried out between 130° and 140° C., and was completed in about three hours. Thereupon, the reaction mixture was diluted with an equal amount of methanol and treated by ion exchange techniques, using Dow Chemical Corporation's "Dowex MSC-1(H)" resin, to remove the catalyst. The ion exchange resin and the diluted material were stirred at ambient temperature until the pH dropped to about 8. The product was then filtered and "stripped" of methanol at 95° C. and thirty mm Hg.

Table 2 depicts the BHMF levels of the BHMFP materials which were propoxylated and evaluated for Freon 11 compatibility. All of these materials met the minimum industry requirement of being compatible with at least thirty grams of Freon 11 per 100 g. polyol. As used herein, "php" means "parts per hundred of polyol".

TABLE 2

| Sample | BHMFP: BHMF, Wt. Pct. | PO:BHMFP, Hydroxyl Equivalent | PO:BHMFP | | Freon 11 Compat., php |
|---|---|---|---|---|---|
| | | | Hydroxyl Number | Visc. @ 25° C. cps, | |
| 2-A | 77.0 | 0.95:1.0 | 389.4 | 735 | 50 |
| 2-B | 39.4 | 0.95:1.0 | 508.4 | 10,800 | 50 |
| 2-C | 29.4 | 0.95:1.0 | 471.6 | 41,000 | 30 |
| 2-D | 27.0 | 1:05:1.0 | 484.1 | 12,200 | 30 |

The foregoing examples illustrate that a BHMFP containing a larger percentage of BHMF itself has a lower hydroxyl number and a greatly reduced viscosity. BHMFP which is high in BHMFP alone, when capped with PO, ultimately contains a relatively high percentage of PO relative to furan moieties, and hence does not have the most desirable flame hazard characteristics.

Examples 2B through 2D show reduced percentages of BHMF in the starting material; the PO adduct hence shows greater viscosity but also, greater potential for imparting reduced flame hazard potential to the final product.

While Example 2D unexpectedly shows lower viscosity than the product of Example 2C, this phenomenon is believed to be explainable in terms of the addition of propylene oxide. Thus, in Example 2D, an excess of PO was added over that provided in the earlier examples. This permits by-products to be formed which contain excess propylene oxide moieties, and which have sufficiently reduced viscosity to serve as a diluent for the remainder of the PO:BHMFP material. Such PO adducts may be illustrated as follows:

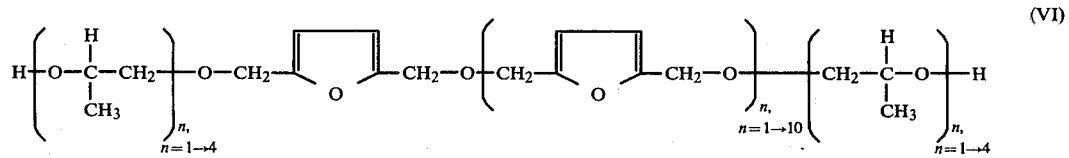

(VI)

-continued

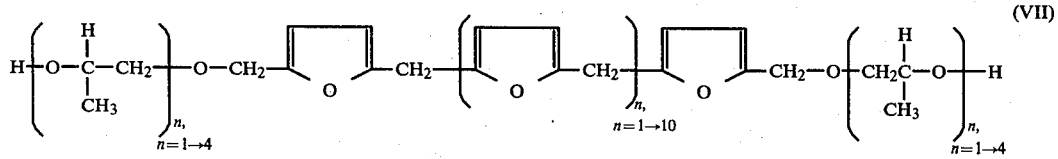

(VII)

EXAMPLE 4

In this example, it was desired to make several rigid urethane foam products using, respectively, the propoxylated materials from Table 2 in Example 3. These materials identified respectively as materials 2-A, 2-B, 2-C and 2-D in Table 2 were suitable for use in the "B" side or component of a rigid urethane foam system, that is, the side which includes the polyol resin, the "Freon" or like blowing agent, the surfactant, and the catalyst(s). These constituents comprise all of the final foam product except the isocyanate portion, which is sometimes referred to as the "A" side. The "B" side is so formulated that, when reacted with a di- or polyfunctional isocyanate, such as polymethyl polyphenyl isocyanate (Upjohn's "Papi" brand isocyanates, for example), a foam with a density of two pounds per cubic foot (2 pcf) is produced. Table 3 depicts the various formulations evaluated.

EXAMPLE 3

Compositions B through F demonstrated the advantages achieveable by propoxylating a known furan-based polyether resin to take advantage of its fire retardancy while at the same time reducing its viscosity to acceptable levels by rendering it compatible with the fluorocarbon used as a blowing agent in the finished urethane foam product. These various foam compositions all contained a high percentage of closed cells, thus making them suitable for use as thermal insulation materials.

In Table 3, the left hand column shows an "A" formulation which consists of a BHMFP material which served as a control. Its characteristics are described in footnote 1. From a consideration of Table 3, it will be noted that, due to incompatability between BHMFP itself and the blowing agent, the latter was blended with the polyisocyanate. The A formulation contains a conventional amount of blowing agent and surfactant, but uses a slightly reduced amount of catalyst relative to the other formulations. This is because the reactive hydroxyl groups in the polymer are primarily hydroxyl groups. For practical application and industry, this polymer, which served as the polyol component of the foam, was really too reactive to be commercially desirable.

The physical properties, particularly compressive strength in relation to density and friability were very satisfactory. Its capability of resisting flame penetration under the USBM test was outstanding. Unfortunately, its closed cell content was only 10%. Consequently, this material was totally unsuited for use as thermal insulation. This failure to process significant closed cell content was believed accounted for by reason of the rapid reaction rate and its attendant excessive exotherm.

Whereas the BHMFP control resin showed the desirability of using a furan based material in a rigid urethane composition for purposes of imparting reduced flame hazard potential thereto, the foam made with an unmodified resin or polyol was not satisfactory. Consequently, compositions embodying the invention are those shown as examples B through F. The data in Table 3 show that, where a high percentage of PO-BHMF is present in the starting material, a relatively low proportion of furan moieties are present in the finished product and the USBM test produces poor results. Likewise, physical properties were not as desirable as those attainable in the foam of Example A. Where, as in Examples C through F, the propoxylated material is low in PO-BHMF, and high in PO-BHMFP, the foams exhibit excellent and, in fact, outstanding physical properties, in excess of 90% closed cell cotent, and particularly, in Examples D, E and F show highly superior results on the USBM flame penetration test. The processability of the foams is very satisfactory, and they are in all other respects very satisfactory for use as thermal insulating material having reduced flame hazard potential.

As has been pointed out, no hologen-containing flame retardent materials comprise any portion of the compositions referred to in Table 3; however, the subject materials may be added to these or similar formulas, if desired.

TABLE 3

| Formulation | A** | B | C | D | E | F |
| --- | --- | --- | --- | --- | --- | --- |
| Stream B: | | | | | | |
| BHMFP[1] | 100 | — | — | — | — | — |
| PO—BHMFP | | | | | | |
| Example 2A | — | 100 | — | — | — | — |
| 2B | — | — | 100 | — | — | — |
| 2C | — | — | — | 100 | — | — |
| 2D | — | — | — | — | 100 | — |
| Mannich Diol (from Example 5) | — | — | — | — | — | 100 |
| Blowing Agent, Freon 11B, g* | 32 | 30 | 30 | 31 | 30 | 30 |
| Surfactant, Q2-5103, g* | 1.5 | 1.5 | 2.0 | 2.5 | 2.0 | 2.0 |
| Catalyst, Polycat 8, g* | 0.8 | 1.0 | 11.0 | 1.0 | 1.5 | — |
| Stream A: (Papi 20)* | 142.9 | 113.0 | 149.9 | 139.0 | 142.7 | 117.3 |
| Index (NCO/OH) | 1.15 | 1.15 | 1.17 | 1.17 | 1.17 | 1.17 |
| Reactivity Profile | | | | | | |
| Reactants, Stream A/B, °F. | 65/70 | 65/70 | 65/70 | 65/70 | 65/70 | 60/60 |
| Cream, sec. | 46 | 30 | 29 | 23 | 38 | 17 |
| Firm, sec. | 70 | — | 60 | 48 | 80 | 42 |
| Tackfree, sec. | 80 | — | 70 | 53 | 100 | 50 |

TABLE 3-continued

| Formulation | A** | B | C | D | E | F |
|---|---|---|---|---|---|---|
| Rise, sec. | 80 | — | 70 | 65 | 90 | 55 |
| Properties |  |  |  |  |  |  |
| Density, pcf | 2.0 | 2.3 | 2.3 | 2.1 | 2.1 | 2.1 |
| Compressive St. Parallel, psi | 38.0 | 25.5 | 38.7 | 38.2 | 40.3 | 28.4 |
| Friability (10 min), pct | 1.0 | 0.0 | 0.0 | 8.0 | 0.7 | 0.0 |
| Closed cell content, pct | 10 | 76 | 92 | 93 | 94 | 92 |
| USBM, sec/pcf | 776 | 41 | 171 | 376 | 545 | 493 |

[1]BHMF polymer having a viscosity of 28,000 cps @ 25° C.
*See test below for identification.
**Non-propoxylated BHMFP is incompatible with Freon 11. The blowing agent was part of stream A in this example only.

In the following example, a propoxylated furfuryl alcohol ("PO-FA") was prepared by techniques known to those skilled in the art, and used as one of the starting materials in the preparation of a so-called Mannich diol. The FA was propoxylated so as to have an average molar ratio of 1.25:1.0, PO:FA, having a normal molecular weight distribution curve, and sometimes merely referred to as "crude" PO-FA, using 0.2% sodium hydroxide as the catalyst, for example.

EXAMPLE 5

To produce a Mannich diol, an active hydrogen compound reacts with an aldehyde such as formaldehyde, and a primary or secondary amine, to create a substituted aminomethyl derivative of the active hydrogen material. In this example, the above PO-FA was used as described below.

A five liter, three-necked flask equipped with mechanical stirrer, heating mantle, reflux condenser and thermometer was charged with 788 g (4.44 mole) of crude (furfuryloxypropan-2-ol,) 146.5 g (4.44 mole) of 91% pure paraformaldehyde, 149.9 g (2.22 mole) of methylamine hydrochloride, and 450 ml of isopropanol. The mixture was stirred and heated to reflux temperature (93°–95° C.) for a period of one hour. Limited heat was required in the initial stages due to the reaction exotherm. After one hour at reflux, all solids had dissolved, and the reaction mixture was a dark brown color. The reaction mixture was subsequently cooled to 10°–20° C., and a solution of 93.2 g (2.33 mole) of sodium hydroxide in 200 ml of deionized water was added dropwise with stirring and cooling, over a period of thirty minutes. When the caustic addition was completed, 25 mm Hg vacuum was applied to the flask, and the isopropanol and water was distilled from the reaction mixture to a final temperature of 85° C. The residue was then cooled to 60° C., and 590 ml of toluene was added with stirring to precipitate the sodium chloride.

After standing overnight at ambient temperature, the sodium chloride was filtered off on a Büchner funnel under vaccuum, and the filter cake rinsed thoroughly with portions of fresh solvent. After drying, the sodium chloride filter cake weighed 137.4 g (105% of the theoretical yield). The toluene filtrate was then returned to the five liter flask, and the toluene distilled off, beginning at a 50 mm Hg level, and gradually being lowered to a 5 mm Hg level. The distillation was complete at a temperature of about 85° C. This left 891 g. of a crude diol (98.2% of theoretical) with a viscosity of 6,000 cps at 25° C., a 399.7 hydroxyl number, a 0.60 acid number and a 0.31% water content. The fluorocarbon compatibility was >50 g per 100 grams of polyol.

The Mannich diol thus produced may be illustrated by the following structure:

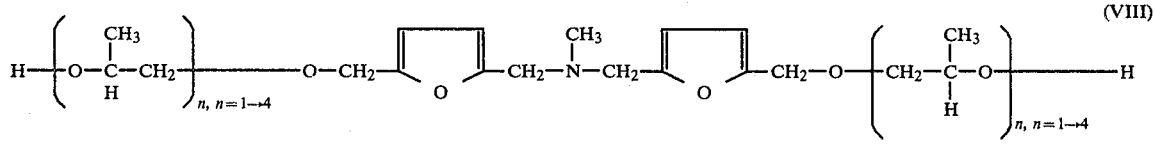

(VIII)

In such formula, where n=1, the compound may be referred to as: N,N-di[5-(methyleneoxypropan-2-ol)furfuryl]methylamine. The commercial product normally contains a predominant portion of the above structure wherein n=1, in both cases, together with reduced amounts of so-called PO homolog compounds wherein n=2, 3 or 4 in either or both portions of the compound.

The structure was confirmed by NMR Spectroscopy. A structural illustration of the preparation of the compound just referred to is as follows:

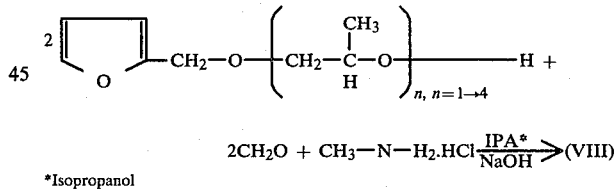

$$2CH_2O + CH_3-N-H_2 \cdot HCl \xrightarrow[NaOH]{IPA^*} (VIII)$$

*Isopropanol

EXAMPLE 6

A Mannich triol having a structure related to that just discussed was prepared along essentially the same lines, as follows:

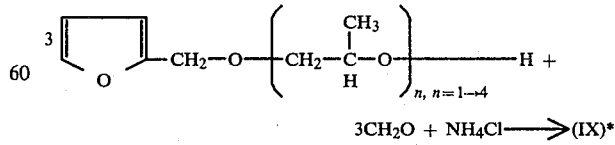

$$3CH_2O + NH_4Cl \longrightarrow (IX)^*$$

*Structure shown below.

A five liter, three-necked flask equipped with mechanical stirrer, heating mantle, reflux condenser and thermometer was charged with 1200 g of crude (furfuryloxypropan-2-ol), 247 g of 91% pure paraformaldehyde, 134 g of ammonium chloride hydrochloride, and 750 ml of isopropanol. The mixture was stirred and heated to reflux temperature (93°-95° C.) for a period of one hour. Limited heat was required in the initial stages due to the reaction exotherm. After one hour at reflux, all solids had dissolved, and the reaction mixture was a dark brown color. The reaction mixture was subsequently cooled to 10°-20° C., and a solution of 105 g of sodium hydroxide in 250 ml of deionized water was added dropwise with stirring and cooling, over a period of thirty minutes. When the caustic addition was completed, 25 mm Hg vacuum was applied to the flask, and the isopropanol and water was distilled from the reaction mixture to a final temperature of 80° C. The residue was then cooled to 60° C., and 1 liter of toluene was added with stirring to precipitate the sodium chloride.

After standing overnight at ambient temperature, the sodium chloride was filtered off on a Büchner funnel under vacuum, and the filter cake rinsed thoroughly with portions of fresh solvent. After drying, the sodium chloride filter cake weighed 147.1 g (100% the theoretical yield). The toluene filtrate was then returned to the five liter flask, and the toluene distilled off, beginning at a 50 mm Hg level, and gradually being lowered to a 5 mm Hg level. The distillation was complete at a temperature of about 85° C. This left 1340.7 g. of a crude triol (102.9% of theoetical) with a viscosity of 61,400 cps at 25° C., a 467.6 hydroxyl number. The fluorocarbon compatibility was 40 g per 100 grams polyol.

The formula of the resulting product may be as follows:

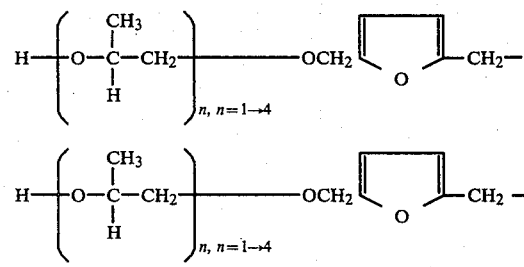

Where n=1 in all cases, the compound may be identified as tris-[5-(methyleneoxypropan-2-ol)furfuryl]amine. Homologous compounds include those wherein n is greater than 1, such compounds being formed by the addition of more than one mole of propylene oxide per terminal hydroxyl group.

EXAMPLE 6

Table 4, which is set forth below, illustrates certain of the ingredients of various isocyanurate foams made according to the invention, and compares a control with foams made respectively from a PO-BHMFP material from Example 2C with two preparations made from a Mannich diol of the type whose preparation was illustrated in Example 4.

TABLE 4

| Formulation | Isocyanurate Foams | | | |
|---|---|---|---|---|
|  | A** | B | C | D |
| BHMFP, g | 15 | — | — | — |
| PO-BHMFP (Example 2C,) g | — | 16.5 | — | — |
| Mannich Diol (Example 6) g | — | — | 15 | 24 |
| Papi 20, g | 100 | 100 | 100 | 100 |
| Surfactant, Q2-5103, g* | 2.5 | 2.5 | 2.5 | 2.5 |

TABLE 4-continued

| Formulation | Isocyanurate Foams | | | |
|---|---|---|---|---|
|  | A** | B | C | D |
| Blowing Agent, F-11B g | 17 | 17 | 17 | 17 |
| Polycat 8, g* | 0.7 | 0.7 | 0.7 | 0.7 |
| Curithane 51, g* | 3.18 | 3.18 | 3.18 | 3.18 |
| Curithane 52, g* | 1.85 | 1.85 | 1.85 | 1.85 |
| Properties |  |  |  |  |
| Density, pcf | 2.0 | 2.0 | 2.1 | 2.1 |
| Compressive St., psi | 35.0 | 30.7 | 35.0 | 31.0 |
| Friability (10 min), pct | 14 | 21 | 24 | 11 |
| K-factor, Btu-in/hr/ft²/°F. | 0.15 | 0.14 | .14 | .14 |
| Flame hazard: |  |  |  |  |
| USBM, sec/pcf | 495 | 1073 | 603 | 752 |

*See text below.
**Non-propoxylated BHMFP is incompatible with Freon 11. The blowing agent was part of stream A in this example only.

From the table above, it will be noted that isocyanurate foams may also be made using the Mannich diols of the invention, as well as the BHMF polymer and the propoxylated BHMF polymer. In the control formation, identified as A above, the blowing agent, various catalysts, a surfactant and an isocyanate were used in the amounts set forth in Column A. The identical amounts were also used in the other formations. 15 parts by weight of a BHMF polymer were used. The isocyanurate foam had the properties listed in Column A, all of which were very acceptable. In Column B, there is illustrated the manufacture of an isocyanurate foam identical to that of formation A, except that the resin is a propoxylated BHMFP such as that referred to in Example 2C of Table 2. This foam, relative to the control, showed somewhat less compression strength and more friability, a slightly improved K-factor, and an outstanding performance on the USBM flame penetration test.

Columns C and D illustrate the preparation of an isocyanurate foam using respectively 15 and 24 parts of the Mannich diol of Example 5, and a formulation otherwise identical to the control. The resulting products had the same density and approximately the same compressive strengths and K-factors. Formation D showed less friability and a better performance on the USBM test, while formation C showed greater friability and a slightly reduced performance on the USBM test. However, the USBM test performance of both products, although less than that of product B, was still exceptional. Consequently, the practicality of using the Mannich diol product in the presence of an isocyanurate foam having a desirably reduced flame hazard potential was clearly demonstrated. While trimerization catalysts were used in all formations summarized in Table 4, there are instances in which the Mannich diol itself may serve as a trimerization catalyst.

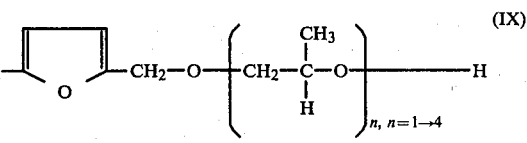

While the above examples do not specifically illustrate the use of the Mannich diol of the invention as a trimerization catalyst, its ability so to act may be demonstrated by the phenyl isocyanate trimerization test. As is known to those skilled in the art, this test comprises adding a particular compound to a 20 times (20×) (weight basis) excess of phenyl isocyanate, and examining the reaction which takes place. If the phenyl isocyanate trimerizes to form an isocyanurate, this may be readily detected, because the isocyanurate is a crystalline product which is insoluble in even an excess of phenyl isocyanate. The Mannich diol of the present invention forms a trimer and, in appropriate formulations, is useful both as a constituent of an isocyanurate foam, and as a catalyst for the reaction by which such foam is made.

EXAMPLE 7

This example illustrates the use of a Mannich triol such as that referred to in Example 6 in preparing a rigid urethane foam having a reduced flame hazard potential.

The same ingredients as those referred to in the examples of Table 3 were used, and the same order of addition was followed, in the preparation of a rigid foam having the following proportions of ingredients, reactivity, and physical properties, respectively.

TABLE 5

| A | [Papi 20* | 135.1 |
|---|---|---|
|   | Mannich Triol, g | 100.0 |
|   | Freon 11*, g | 35.0 |
| B | Polycat 8*, g | 1.0 |
|   | Silicone Surfactant Q2-5103* | 1.5 |
|   | Index | 1.15 |
| Reactivity |  |  |
| Processing temperature, A/B, °F. |  | 70/65 |
| Cream, sec. |  | 45 |
| Firm, sec. |  | 120 |
| Tack-free, sec |  | 130 |
| Rise, sec. |  | 150 |
| Density, pcf |  | 2.0 |
| Compressive Strength, Parallel, psi |  | 33.7 |
| Friability (10 min), pct |  | 3.2 |
| Closed Cell Content, pct |  | 84 |
| USBM, sec/pcf |  | 155 |

*see text below.

From the foregoing table, it is apparent that a rigid foam product was able to be made which, while not superior to some of the other illustrated foams, was nevertheless satisfactory from the standpoint of the USBM flame penetration test, and from the standpoint of closed cell percentage, friability and compressive strength. A foam of this type, having density of about 2.0 pcf, is, therefore, also suitable for use as thermal insulation.

Identification of Reaction Constituents

In the above tables and elsewhere in the examples, reference is made to various compositions of the mixture used to make the foam. As pointed out, these ingredients are typical in those compositions known to those skilled in the art to be useful in making rigid urethane or isocyanurate foams. The identity of certain of the specific materials referred to above is as follows:

"Freon 11" is fluorotrichloromethane (DuPont Corp.—Wilmington, Del.);

"Polycat 8" is dimethyl cyclohexyl amine (Abbott Labs—Northern Chicago, Ill.);

"Papi 20" is polymethyl polyphenyl isocyanate (Upjohn Co.—Kalamazoo, Mich.);

"Q2-5103" is a silicone glycol polymer surfactant (Dow Corning Silicones—Midland, Mich.);

"Curithane 51" is a tertiary amine trimerization catalyst (also supplied by Upjohn Co.—Kalamazoo, Mich.);

"Curithane 52" is a tertiary amine trimerization catalyst (also supplied by Upjohn Co.—Kalamazoo, Michigan).

Basically, the above examples describe the production and use of furan-based materials, and specifically products derived from BHMF, which have the advantages of forming a flame resistant char in urethane and isocyanaurate compositions. The novel products are propoxylated to render them compatible with Freon, which in turn makes them capable of dilution to workable viscosities by Freon for use in commercial foam forming systems. In addition to the various compositions identified above by Nos. I-IX, namely, BHMF and its homopolymers, propoxylated BHMF, and propoxylated polymers of BHMF, there were illustrated both Mannich diol and Mannich triol novel products.

The invention also comprehends the use of compositions having other, slightly different molecular structures, and mixtures of such compounds. Compounds made according to the present invention may be referred to in the most general sense as having three moieties. These parts or moieties are referred to in the illustration set forth below, and in the claims, as being a propylene oxide terminated bis(hydroxymethyl) furan derivative called the "A" group; a center or "B" group which may structurally be the bis(hydroxymethyl) furan or methyl furan, radical or which may be one of several amino groups, with or without the 5-methyl furfuryl alcohol radical.

The B substituents may be difunctional, as where the R group is based on methyl furan or bis(hydroxymethyl)furan radical or on a difunctional amino group of the type illustrated below, or may be tri- or tetra-functional, as for example where the R group is a diamine having three or four available reaction sites. The C or right hand group includes a terminal hydroxyl group and is based on propylene oxide or a polymer thereof. The most general structural formula is as follows:

"A"      "B"      "C"

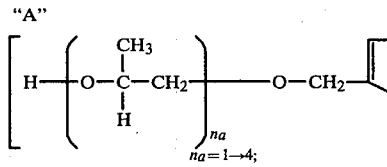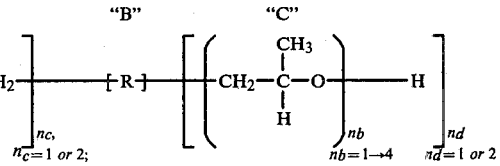

In summary, the products of the invention are materials which contain a substantial furan-based moiety, which are hydroxyl-terminated, and which may include polymers of BHMF or certain amines. In the above general formulation, the following substitutions may be made:

$R = -O-;$

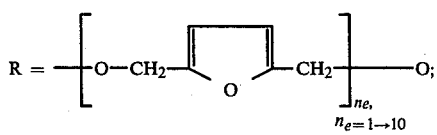

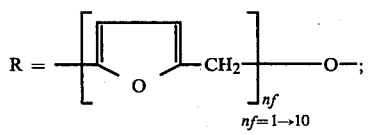

$R = -\overset{L}{\underset{|}{N}}-M$, where L = lower alkyl or M; and

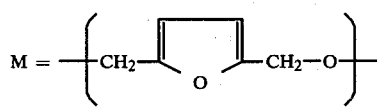

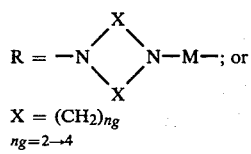

$X = (CH_2)_{ng}$
$ng = 2 \rightarrow 4$

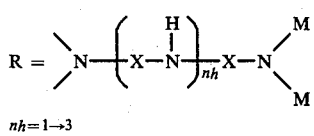

$nh = 1 \rightarrow 3$

While the substitutions set forth above illustrate a range of useful compositions, it is generally preferred that the resulting compound be relatively rich in furan; consequently, $n_e$ and $n_f$ are preferably about 3 to 6, while $n_a$ and $n_b$ are preferably equal to 1 or just greater than 1, on the average. Likewise, when R is an amine, it may have two or more nitrogens, and theoretically might have a significantly larger number; however, the preferred compositions are those which have relatively fewer nitrogens and a relatively more furan content.

In a number of the foregoing examples, particularly including those examples in which compounds referred to as polymers and propoxylated polymers of BHMF were identified, a description was made of several particular molecular structures. As is known to those skilled in the polymer and synthetic resin art, however, the actual commercial products with which the invention is concerned are resinous products which actually consist of mixtures of a number of individual compounds.

In other words, for example, an actual composition will almost certainly contain individual molecules differing from one another in molecular weight. The commercial composition will, for example, include a certain percentage of BHMF polymers of two different types, that is, it will comprise the type shown as having structure VI, as well as the type having structure VII. Further, the same situation applies to propoxylated BHMF polymers. Consequently, herein and in the appended claims, the expressions refer not only to an exact chemical compound, but to individual compositions and mixtures thereof having, on the average, certain molecular weight, certain functionality, etc. Therefore, while it is possible to identify individual compounds having defined structure, this is not normally done in practice, as it is not necessary or desirable.

The invention may thus be seen to be directed to novel furan-based compositions of the type outlined above, having terminal hydroxyl groups and being able to form active components of rigid urethane and isocynanurate compositions demonstrating a reduced flame hazard potential in relation to prior known compositions, while at the same time being compatible with other known constituents of urethane- and isocynanurate-forming materials.

It will thus be seen that the present invention provides novel chemical compositions having a number of advantages and characteristics, including those pointed out above and others which are inherent in the invention. The invention having been described by way of numerous examples, is anticipated that changes and modifications of the described chemical compositions will occur to those skilled in the art, and that such changes and modifications may be made without departing from the spirit of the invention or the scope of the appended claims.

I claim:

1. A method of trimerizing a composition which includes a polyfunctional isocyanate component and a polyfunctional polyol composition, said method including adding to said composition from about 0.5% to about 40% by weight of a Mannich diol composition adapted to serve, at least in part, as a trimerizing catalyst for said composition, and having the formula:

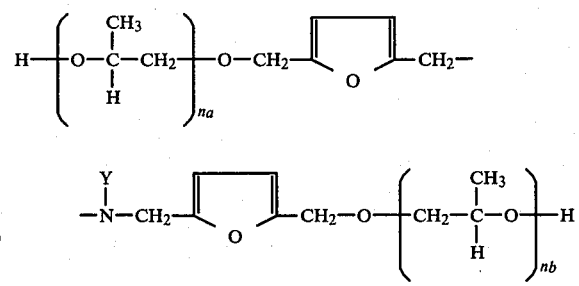

wherein $n_a$ is from 1 to 4, $n_b$ is 1 to 4, and wherein X is a $C_1$–$C_6$ alkyl group and permitting said components to react to from an isocyanurate-containing composition.

2. A rigid polyurethane foam composition comprising the reaction product of about 100 parts of a chemical compositions consisting essentially of one or more compounds having the formula:

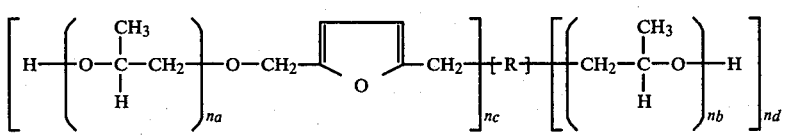

wherein $n_a$ is from 1 to about 4, wherein $n_b$ is from 1 to about 4, wherein $n_c$ is 1 or 2, wherein $n_d$ is 1 or 2, and wherein $R = -O-$;

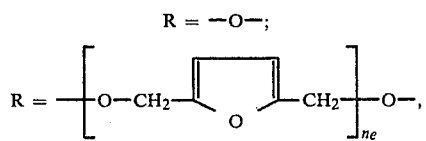

and $n_e$ is from 1 to 10;

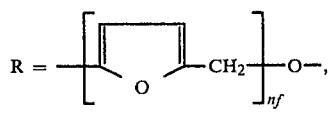

and $n_f$ is from 1 to 10;

where L is lower alkyl or M, and M is

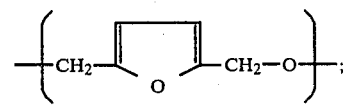

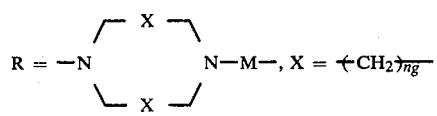

and $n_g$ is from 2 to 4; or

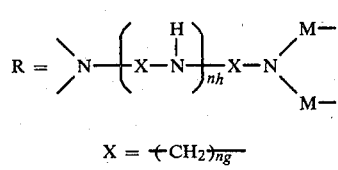

$X = +CH_2\overline{)_{ng}}$ $n_g$ is 2 to 6, and $n_h$ is from 1 to 3, and from about 100% to about 120% of a stoichiometric amount of a reactive polyisocyanate, said composition containing a fluorocarbon material as a blowing agent, and having a density of from 1.5 to about 5 compounds per cubic foot.

3. A composition as defined in claim 2 wherein $n_a$ and $n_b$ are from about 1 to about 2.

4. A composition as defined in claim 2 wherein $n_a$ and $n_b$ are 2 or less and $R=-O-$.

5. A composition as defined in claim 2 wherein $n_a$ and $n_b$ are 2 or less and wherein $R = O-$; or -continued

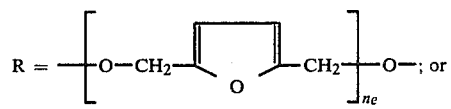

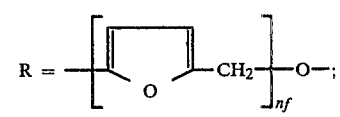

and $n_e$ or $n_f$ are from about 1 to about 6.

6. A composition as defined in claim 2 wherein $n_a$ and $n_b$ are from about 1 to about 2 and wherein

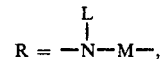

where L is lower alkyl or M and

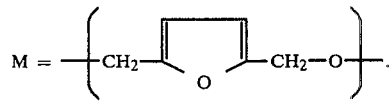

7. A composition as defined in claim 2 wherein $n_a$ and $n_b$ are from 1 to about 2, and wherein

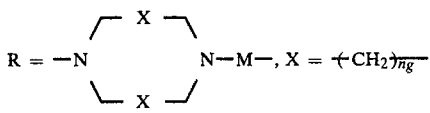

and $n_g$ is from 2 to 4; or

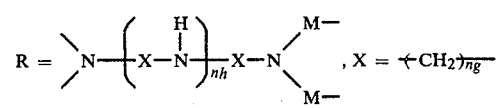

is from 2 to 6 and $n_h$ is from 1 to 3.

8. A composition as defined in claim 2 wherein $n_a$ and $n_b$, on the average, are from 1 to about 2, and wherein

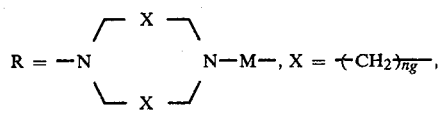

and $n_g$ is 2.

9. A rigid isocyanurate foam composition comprising the reaction product of about 100 parts of a chemical composition consisting essentially of one or more compounds having the formula:

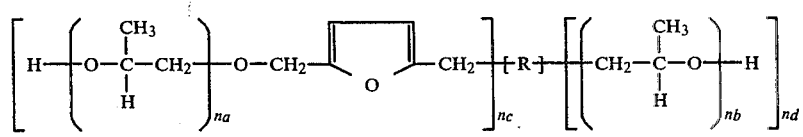

where $n_a$ is from 1 to about 4, wherein $n_b$ is from 1 to about 4, wherein $n_c$ is 1 or 2, where $n_d$ is 1 or 2, and wherein $R = -O-$;

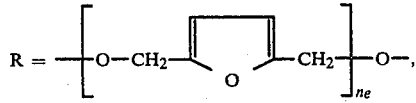

and $n_e$ is from 1 to 10;

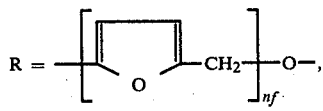

and $n_f$ is from 1 to 10;

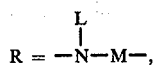

and L is lower alkyl or M and M is

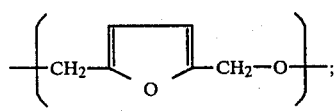

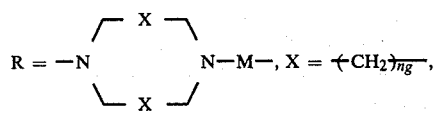

and $n_g$ is from 2 to 4; or

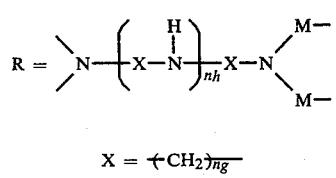

$X = +CH_2)_{\overline{ng}}$ $n_g$ is 2 to 6, and $n_h$ is from 1 to 3; and from at least 120% to about 500% of a stoichiometric amount of a reactive polyisocyanate, said composition containing a fluorocarbon material as a blowing agent, and having a density of from 1.5 to about 5 pounds per cubic foot.

10. A composition as defined in claim 9 wherein $n_a$ and $n_b$ are from about 1 to about 2.

11. A composition as defined in claim 9 wherein $n_a$ and $n_b$ are 2 or less and R is —O—.

12. A composition as defined in claim 9 wherein $n_a$ and $n_b$ are 2 or less and wherein R is —O—; or

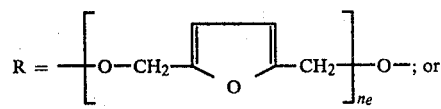

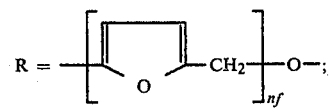

and $n_e$ or $n_f$ are from about 1 to about 6.

13. A composition as defined in claim 9 wherein $n_a$ and $n_b$ are from about 1 to about 2 and wherein

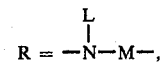

where L is lower alkyl or M and

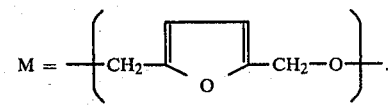

14. A composition as defined in claim 9 wherein $n_a$ and $n_b$ are from 1 to about 2, and wherein

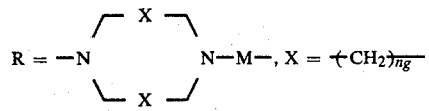

and $n_g$ is from 2 to 4; or

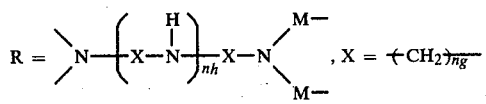

$n_g$ is from 2 to 6 and $n_h$ is from 1 to 3.

15. A composition as defined in claim 9 wherein $n_a$ and $n_b$, on the average, are from 1 to about 2 and wherein

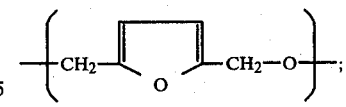

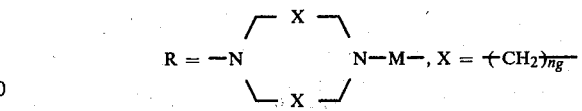

16. A method of decreasing the flame hazard potential of a rigid urethane or isocyanurate foam composition, said method comprising adding to a urethane- or isocyanurate-forming ingredients a composition consisting essentially of one or more compounds having the formula:

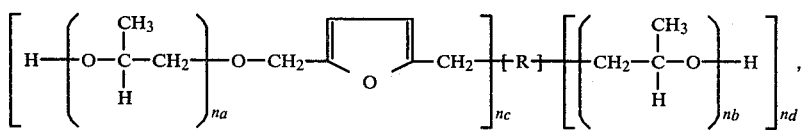

wherein $n_a$ is from 1 to about 4, wherein $n_b$ is from 1 to about 4, wherein $n_c$ is 1 or 2, wherein $n_d$ is 1 or 2, and wherein $R = -O-;$

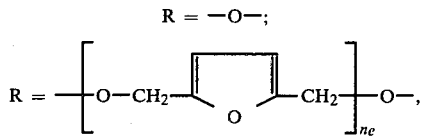

and $n_e$ is from 1 to 10;

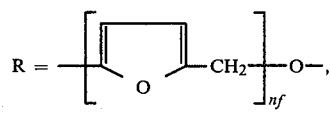

and $n_f$ is from 1 to 10;

$$R = -\overset{\underset{|}{L}}{N}-M-,$$

where L is lower alkyl or M, and M is

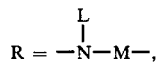

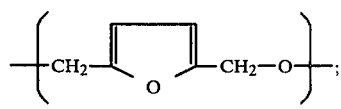

and $n_g$ is 2 to 4; or

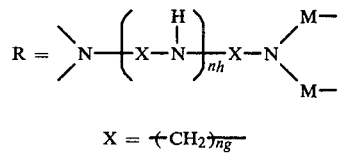

$X = \text{\textendash}(CH_2)_{\overline{ng}}$ $n_g$ is 2 to 6, and $n_h$ is from 1 to 3, and, utilizing said composition as at least a portion of the polyol component of said composition, permitting the ingredients thereof to react in order to form a modified polyurethane or isocyanurate composition having decreased flame hazard potential.

17. A method as defined in claim 16 wherein $n_a$ and $n_b$ are from about 1 to about 2.

18. A method as defined in claim 16 wherein $n_a$ and $n_b$ are 2 or less and $R=-O-$.

19. A method as defined in claim 16 wherein $n_a$ and $n_b$ are 2 or less and wherein $R = O-;$ or

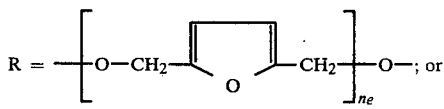

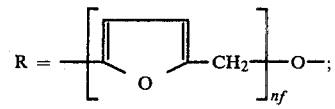

and $n_e$ or $n_f$ are from about 1 to about 6.

20. A method as defined in claim 16 wherein $n_a$ and $n_b$ are from about 1 to about 2 and wherein

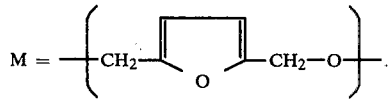

where L is lower alkyl or M and $$R = -\overset{\underset{|}{L}}{N}-M-,$$

21. A method as defined in claim 16 wherein $n_a$ and $n_b$ are from 1 to about 2, and wherein

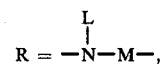

and $n_g$ is from 2 to 4; or

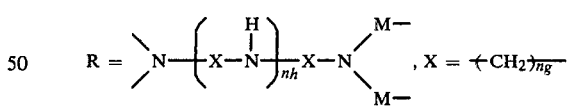

$n_g$ is from 2 to 6 and $n_h$ is from 1 to 3.

22. A method as defined in claim 16 wherein $n_a$ and $n_b$, on the average, are from 1 to about 2, and wherein

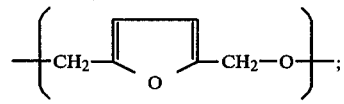

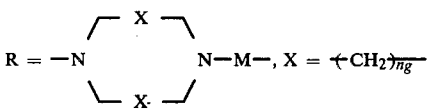

* * * * *